(12) United States Patent
Aldenkortt

(10) Patent No.: US 7,339,073 B2
(45) Date of Patent: Mar. 4, 2008

(54) METHOD FOR OBTAINING 5-HALOGENOLAEVULINIC ACID ALKYL ESTERS

(76) Inventor: Sven Aldenkortt, Lindenstr. 19, 97956 Wenkheim (DE)

( * ) Notice: Subject to any disclaimer, the term of this patent is extended or adjusted under 35 U.S.C. 154(b) by 461 days.

(21) Appl. No.: 10/496,591

(22) PCT Filed: Nov. 22, 2002

(86) PCT No.: PCT/DE02/04302

§ 371 (c)(1),
(2), (4) Date: Oct. 28, 2004

(87) PCT Pub. No.: WO03/045895

PCT Pub. Date: Jun. 5, 2003

(65) Prior Publication Data

US 2005/0070727 A1    Mar. 31, 2005

(30) Foreign Application Priority Data

Nov. 23, 2001  (DE) .................... 101 57 557

(51) Int. Cl.
*C07C 69/66*    (2006.01)
*C07C 59/00*    (2006.01)
(52) U.S. Cl. ............... 560/174; 560/179; 560/184; 562/579; 562/586
(58) Field of Classification Search .......... None
See application file for complete search history.

(56) References Cited

U.S. PATENT DOCUMENTS 3,275,504 A * 9/1966 Herschler ................ 504/152
5,907,058 A * 5/1999 Moens ..................... 562/567

OTHER PUBLICATIONS

MacDonald, S.F., Methyl 5-Bromovevulinate. Canadian Journal of Chemistry, 1974, vol. 52, p. 3257-3258.*
Ha et al. Selective Bromination of Ketones. A Convenient Synthesis of 5-Aminolevulinic Acid. Synthetic Communications, 1994, vol. 24 (18), p. 2557-2562□□.*

* cited by examiner

*Primary Examiner*—Sikarl A. Witherspoon
(74) *Attorney, Agent, or Firm*—Edwin D. Schindler

(57) ABSTRACT

A method for obtaining a 5-bromolevulinic acid methyl ester or a 5-chlorolevulinic acid methyl ester from either a bromination mixture or a chlorination mixture, containing either a 5-bromo-levulinic acid methyl ester or a 5-chlorolevulinic acid methyl ester, respectively, produced by either brominating or chlorinating levulinic acid or a levulinic acid methyl ester, and further including the steps of dissolving the bromination or chlorination mixture in an organic solvent or solvent mixture and cooling the solution, preferably to −20° C.−−40° C., with the 5-bromolevulinic acid methyl ester or 5-chlorolaevulinic acid methyl ester being crystallized out of the solution. The 5-bromolevulinic acid methyl ester or 5-chlorolevulinic acid is then isolated by draining off the solution with the remaining bromination mixture or chlorination mixture, as appropriate.

16 Claims, No Drawings

METHOD FOR OBTAINING 5-HALOGENOLAEVULINIC ACID ALKYL ESTERS

BACKGROUND OF THE INVENTION

1. Field of the Invention

This is a 371 of PCT/DE02/04302, filed Nov. 22, 2002, and published as WO 03/045895 on Jun. 5, 2003.

The invention relates to a process for obtaining 5-bromo levulinic acid methyl ester from a bromination mixture, which is obtained by bromination of levulinic acid or levulinic acid methyl ester and which contains 5-bromolevulinic acid methyl ester, and to a process for obtaining 5-chlorolevulinic acid alkyl esters.

The bromination of levulinic acid in methanol with one mol equivalent of bromine yields 1. 3-bromolevulinic acid methyl ester
2. 5-bromolevulinic acid methyl ester
3. 3,5-bromolevulinic acid methyl ester and as a result of the consumption of further bromine equivalents for the formation of 3,5-bromolevulinic acid methyl ester from (1) and/or (2)

4. the not brominated levulinic acid methyl ester.

The quantity ratio of the products within the bromination mixture behaves like (1):(2):(3):(4)=28:56:8:8, whereas insignificant variations may occur according to the reaction conditions. In general, however, the selectivity of the formation of the bromination products, especially the 5-bromolevulinic acid methyl ester, can not decisively be changed. The bromination of levulinic acid methyl ester (4) instead of levulinic acid with one equivalent of bromine in methanol leads approximately to the same result.

2. Description of the Prior Art

Therefore, the production of 5-bromolevulinic acid methyl ester depends on the mentioned bromination mixture. According to the latest development of the technology, several processes for the isolation of the 5-bromolevulinic acid methyl ester from the bromination mixture are known.

S. F. McDonald in Can. J. Chem. 1974, 52, 3257–3258 describes a process, from which the mentioned bromine compound is obtained from the bromination mixture by double fractional high vacuo distillation. In this way the 5-bromolevulinic acid methyl ester is obtained (relating to the starting compound levulinic acid) in 30% yield and about 2% of the 3,5-dibromolevulinic acid methyl ester as an impurity.

To prevent an acid catalysed change of the ratio of the isomers, the destination should proceed quickly and the thermal stress of the bromination mixture should be kept as low as possible. A higher thermal strain particularly has a problematic effect if traces of hydrogen bromide are present, which cause an unfavourable change of the yield to the disadvantage of the 5-bromolevulinic acid methyl ester. The experience also showed, that the amount of the 5-bromolevulinic acid methyl ester obtained by fractional distillation, considerably decreases, if small amounts of the 3,5-dibromolevulinic acid methyl ester are present.

The requirements for the careful production of the desired ester connected with an optimal yield are met only unsufficiently, since the double fractional distillation causes a comparable high expenditure of time resulting in a high thermal strain of the distillation mixture.

Moreover, if the range of pressure needed for the distillation is not reached within a short period of time, the destination time is lengthend and on top the thermal strain of the bromination mixture increases.

On top of that, it especially has to be considered as a disadvantage, that the separation of the brominated products by distillation according to the available process all in all is very expensive, because for this a double fractional distillation using a vacuum jacketed vigreux column is necessary. Because of the high technical expense, this process is ruled out for a large-scale application.

H.-J. Ha, S.-K. Lee, Y.-J. Ha, J. W. Park, Synth. Comm. 1994, 24(18), 2557–2562 describe a process for obtaining 5-bromolevulinic acid methyl ester, which provides the desired ester from the bromination mixture by means of column chromatography. High costs are connected in an unfavourable manner to this process and therefore a purification using liquid chromatography is out of question when you consider a technical application.

With regard to the use of 5-bromolevulinic acid methyl ester, production processes for the preparation of 5-aminolevulinic acid hydrochloride must be mentioned in the latest development of the technology.

American patent U.S. Pat. No. 5,907,058 shows a process in which 5-aminolevulinic acid hydrochloride is prepared by processing 5-bromolevulinic acid methyl ester with sodium diformylamide in water-free acetonitrile and the following acid catalysed hydrolysis of the resulting 5-diformylamino levulinic acid methyl ester.

In the Z. Naturforsch. 1986, 41b, 1593–1594 a process is described by E. Benedikt and H.-P. Köst, which is characterised by the following steps: Processing of 5-bromolevulinic acid methyl ester together with potassium phthalimide in dimethylforamide yielding 5-phthalimido levulinic acid methyl ester, which is then hydrolised by an acid.

Finally, in the above mentioned publication of H.-J. Ha, S.-K. Lee, Y.-J. Ha, J. W. Park, Synth. Comm. 1994, 24(18), 2557–2562, a process for the preparation of 5-aminolevulinic acid hydrochloride is described. This process starts with 5-bromolevulinic acid methyl ester, which is prepared from levulinic acid by bromination, and which is characterised by the following process steps: Processing of 5-bromolevulinic acid methyl ester together with sodium azide in dimethyl formamide to 5-azidolevulinic acid methyl ester and followed by the catalytic hydrogenation and the subsequent ester hydrolysis of the formed 5-aminolevulinic acid methyl ester hydrochloride.

The disadvantage of these processes is, that they require the starting material in high purity. The herewith connected high technical expense and the high costs for the preparation of this product lead to the fact, that a large-scale production of 5-aminolevulinic acid hydrochloride like mentioned above is unprofitable so far.

SUMMARY OF THE INVENTION

Considering this background, an object of the present invention is to provide a process for the preparation of 5-bromolevulinic acid methyl ester, which avoids the mentioned disadvantages, and which allows for the production of the mentioned substance in high purity and therefore is suitable for a large-scale application, which leads to a cost-effective preparation of the mentioned substance and which, therefore, meets the requirement for a cost-effective preparation of 5-aminolevulinic acid methyl ester hydrochloride and 5-aminolevulinic acid hydrochloride. Further, inventive process includes the recycling of the resulting undesirable byproducts.

According to the invention the problem is solved by a process, which intends to use the following process steps:
- dissolving the bromination mixture in an organic solvent or solvent mixture
- cooling down the solution to low temperatures, preferably to temperatures which are lower than −20° C., especially in the temperature range between −20° C. to −40° C.
- crystallisation of the 5-bromolevulinic acid methyl ester out of the solution
- isolation of the crystalline 5-bromolevulinic acid methyl ester by draining off the solution with the remaining bromination mixture.

The suggested process starts from known processes for the preparation of 5-bromolevulinic acid methyl ester, which yields a mixture of 3-bromolevulinic acid methyl ester, 5-bromolevulinic methyl ester, 3,5-bromolevulinic acid methyl ester and levulinic acid methyl ester by means of bromination of levulinic acid and levulinic acid methyl ester.

To isolate the 5-bromolevulinic acid methyl ester from a mixture according to the present invention, the mixture will be dissolved in an organic solvent or solvent mixture first and cooled down in the following process step. During this procedure, temperatures in the range of −20° C. and −40° C. must be kept. Thereby, the 5-bromolevulinic acid methyl ester crystallises in the form of colorless needles or plates, whereas the other parts of the bromination mixture remain in the solution. To seperate the crystallised ester from the rest of the bromination mixture, the remaining solution is simply drained off.

The basis of the invention is essentially the finding, that the single parts of the bromination mixture in solution show a completely different crystallisation behavior. This behavior proved to be extremely selective, where in the given temperature range between −20° C. and −40° C. only the 5-bromolevulinic acid methyl ester crystallises. By cooling the mixture down to this temperatures it is made secure that only the before mentioned bromination compound precipitates. The suggested procedure shows a yield of 35% to 38% in relation to the quantity of levulinic acid, whereby the produced bromination product has a high purity of 99%. Impurities consist after the isolation of the 5-bromolevulinic acid methyl ester of levulinic acid methyl ester and 3-bromolevulinic acid methyl ester. These two compounds don't disturb further synthesis steps, whereas the 5-bromolevulinic acid methyl ester gained according to the procedure of McDonald as mentioned above contains 3,5-dibromolevulinic acid methyl ester as an impurity. This compound affects the further reaction steps extremly unfavourable and makes complicated purification procedures of the final product necessary! The production process according to the given invention must be considered as extremely gentle, since the bromination mixture and the ester to be isolated are not exposed to thermal strain by the crystallisation process. The danger of the acid catalysed change of the ratio of the isomers is thus excluded in a favourable manner. An essential advantage of the procedure according to the invention are its extremely simple courses in the production of the 5-bromolevulinic acid methyl ester, which can accordingly be carried out quickly. The mentioned procedure steps may be applied not only in the laboratory but in large-scale installations just in the same. The costs for the technical process installations in relation to the produced amount of the ester and the production costs are much lower than the corresponding expenses for the procedure according to the latest development of the technology using liquid chromatography or high vacuo distillations.

Several organic solvents or solvent mixtures are suitable for carrying out the selective crystallisation. According to the present invention are recommended:
- the solvents
  - ethanol
  - 2-propanol
  - diisopropyl ether
- or the solvent mixtures
  - diethyl ether plus lower or higher boiling petroleum ether fractions and/or
  - t-butyl methyl ether plus petroleum ether and/or
  - diethyl ether plus cyclohexane and/or
  - t-butyl methyl ether plus cyclohexane.

In the laboratory experiments mixtures of petroleum ether (30–50° C.) and diethyl ether or tert-butyl methyl ether in a ratio of 1:1 proved to be reliable. The amount of solvents necessary for the carrying out of the process are relatively low.

A further advantage of the procedure according to the invention shows when the respective byproducts must be disposed of. According to a feature of the invention it is planned to recycle the remaining bromination mixture after the crystallisation of the 5-bromolevulinic acid methyl ester. The remaining mixture contains
1. 3-bromolevulinic acid methyl ester
2. rests of 5-bromolevulinic acid methyl ester
3. 3,5-bromolevulinic acid methyl ester
4. and levulinic acid methyl ester.

By this the products 1.–3. can be converted to levulinic acid methyl ester by catalytic hydrogenation with hydrogen. For this purpose the mixture is dissolved in methanol and reduced in the presence of a hydrogenation catalyst by passing in hydrogen at a pressure of 20 bar.

The levulinic acid methyl ester recovered in this way can then be used as a starting product for the production of the mentioned bromination mixture. For this purpose the levulinic acid methyl ester is dissolved in methanol and is converted like in the above mentioned bromination of levulinic acid methyl ester with elemental bromine into the bromination mixture. This conversion nearly yields the same mixture of isomers as the bromination of levulinic acid. The mixture contains especially 5-bromolevulinic acid methyl ester in a high concentration and can so be used with advantage as a starting product for the procedure according to the invention.

As a catalyst palladium on carbon is suggested according to the given invention. The advantage of this catalyst is that it can be regenerated after the hydrogenation reaction.

When the hydrogenation of the remaining bromination mixture is made hydrogen bromide is the only byproduct. This product can be disposed of without problems when it is converted to carbon dioxide, water and sodium bromide by sodium hydrogen carbonate. The given invention shows respective steps for the procedure. A cost-intensive and/or the environmentally harmful disposal of byproducts is not necessary at all in the production of 5-bromolevulinic acid methyl ester according to the procedure invented.

The low-cost production of 5-bromolevulinic acid methyl ester according to the given invention opens up a wide range of application possibilities of the given ester. According to the invention especially the use for the production of 5-aminolevulinic acid methyl ester hydrochloride and the thereof gained 5-aminolevulinic acid hydrochloride is intended. The last mentioned compound is used for the cancer diagnosis and for the therapy of carcinomas as well, especially for bladder cancer carcinomas. On top, 5-aminolevulinic acid hydrochloride is used as a broad spectrum herbicide in the agricultural sector. Since this substance occurs in nature itself, this herbicide has the advantageous characteristic that it is biodegredable and doesn't provide unnatural and problematic metabolites.

DETAILED DESCRIPTION OF THE PREFERRED EMBODIMENTS

A large-scale production of 5-aminolevulinic acid hydrochloride failed until now, inspite of intensive efforts because the costs for the production of the starting product were to high. Up to the present moment the substance is therefore produced only in small quantities which results in the disadvantage of high prices. One gram of the substance costs today on the chemical market about 30 to 50 ∈ and in medical quality 75 ∈. A broad application of 5-aminolevulinic acid hydrochloride in agriculture is not possible because the prices are to high. The low-cost production of 5-bromolevulinic acid methyl ester according to the given invention therefore provides the conditions for a large-scale production of 5-aminolevulinic acid hydrochloride. The use according to the invention according to the proposed procedure produced 5-bromolevulinic acid methyl ester for the production of 5-aminolevulinic acid hydrochloride also contains the use of procedures described in the latest developments of the technology.

When using 5-bromolevulinic acid methyl ester for the production of 5-aminolevulinic acid hydrochloride it is according to the invention especially suggested, that the last process step for the production of 5-bromolevulinic acid methyl ester is directly connected to the first process step for the production of 5-aminolevulinic acid hydrochloride without changing the reaction vessel.

In the usual synthesis of 5-aminolevulinic acid hydrochloride 5-bromolevulinic acid methyl ester is a liquid. In this form it shows strongly lachrymatory and skin irritating properties, every contact with the substance must therefore be avoided. The crystalline form of the bromination product however shows less irritating features. If the product is left in the reaction vessel after crystallisation for the carrying out of the following processes a contact with people is avoided a priori. The danger of eye and skin irritations is so completely excluded.

By the proposed procedure a further advantage is obtained which is based in the omission of a storing of the 5-bromolevulinic acid methyl ester and the problems connected. The brominated compound tends in the presence of traces of acid—for example hydrogen bromide—to an acid catalised isomerisation in the compounds 3-bromo-, 3,5-dibromo- and levulinic acid methyl ester. It therefore usually requires a careful storing, which, however, is excluded in the given procedure.

On top, the two following steps from 5-bromolevulinic acid methyl ester to 5-aminolevulinic acid hydrochloride run at already 20° C. to 25° C. (from time to time even exotherm) so that no energy is required and the reaction mixtures must only be stirred.

In an alternative, preferred embodiment, a further production procedure is mentioned. 5-bromolevulinic acid methyl ester and 5-chlorolevulinic acid esters are starting compounds for the production of the pharmacologically important substance 5-aminolevulinic acid hydrochloride.

According to the latest developments in the technology the production of the 5-bromolevulinic acid methyl ester is considered difficult because of the cost-intensive work-up of the production mixture by means of distillation and chromatography. Hereby, especially the strongly lachrymatory properties of the liquid 5-bromolevulinic acid methyl ester proved to be disadvantageous. The lachrymatory feature is hereby a result of the bromo methyl ketone moiety in the compound and is valid in general for compounds containing such a moiety as a structural element in the molecule (comp. for example M. Gaudry, A. Marquet, Organic Syntheses, Coll. Vol. 6, 193–195).

To exclude the declared disadvantages of the 5-bromo compounds and to produce more stable, not lachrymatory, storable—at the C-5 position halogen substituted derivates—instead of the 5-bromo compounds the 5-chloro or 5-iodo compounds are suitable. The 5-chloro compounds don't possess lachrymatory properties in comparison to the 5-bromo compounds, because they have a chloro methyl ketone moiety instead of a bromo methyl ketone moiety. On top, they are thermically much more stable in comparison to the bromo compounds and don't tend under the conditions of the distillation to acid catalised isomerisations. This feature is also valid for other chloro methyl ketones (comp. E. Warnhoff, M. Rampersad, P. S. Raman, F. W. Yerhoff, Tetrahedron Lett. 1978, 19, 1659–1662).

The production of chloro esters of the levulinc acid, which are substituted at the C-5 position by direct chlorination of levulinic acid or esters thereof with or without an organic thinner by passing in chlorine gas has the disadvantage that you receive—in comparison to the bromination with elemental bromine—a strongly reduced selectivity of the halogenation to the disadvantage of the desired 5-chloro compounds. For example the chlorination of levulinic acid leads to such a strongly reduced selectivity that you receive as a main product 3-chloro levulinic acid. Besides not desired poly chlorination products as 3,3-dichloro-, 3,5-dichloro-, 5,5-dichlorolevulinic acid emerge as well as further unknown products together with the not converted levulinic acid (comp. EP 0397048). In analogy to this you receive substance mixtures approximately corresponding to the above mentioned when you try to chlorinate levulinic acid esters under the most different conditions. It is very difficult to separate these substance mixtures, the yields are bad and they are therefore not usual for further conversions. When you chlorinate levulinic acid ethyl ester without thinners you receive for example mainly the 3-chlorolevulinic acid ethyl ester. The chlorination of levulinic acid ethyl ester with sulphuryl chloride in an unpolar organic solvent yields with the reverse selectivity mainly the 3-chlorolevulinic acid derivative (comp. EP 0397048).

In EP 58392 a procedure for the production of 5-chlorolevulinic acid ethyl ester is described that starts from succinic acid mono ethyl ester mono chloride. This compound is converted with diazo methane at −5° C. and is after that worked up by passing in hydrogen chloride. You receive so the desired compound in pure form and in a high yield but the difficult handling of explosive diazo methane makes this method for the large-scale use not suitable. The same procedure is described in PL 136454. Instead of the succinic acid mono ethyl ester mono chloride the respective methyl ester derivative is used and results in the formation of 5-chlorolevulinic acid methyl ester.

The 5-chlorolevulinic acid alkyl esters are starting compounds for the production of other substances and are further converted by the nucleophilic substitution of the halogen atom.

Besides alkali imides and alkali azides tertiary amines are suitable nucleophiles. The tertiary amine hexamethylene tetramine(urotropine) is described as a cheap and commercially available nucleophilic reagent for the introduction of the amino group, for example in bromo methyl ketones (comp. N. Blazevic, D. Kolbah, B. Berlin, V. Šunjic, F. Kajfez, Synthesis, 1979, 161–176).

The conversion of 5-chlorolevulinic acid methyl ester with urotropine results in 5-urotropiniumlevulinic methyl ester chloride, a quarternary ammonium salt of the levulinic acid methyl ester that in connection with this invention has been produced for the first time and directly been converted to 5-aminolevulinic acid hydrochloride. In WO 02/32852A2 the production of 5-urotropiniumlevulinic esters from 5-bromolevulinic acid esters (chain lengths of the ester alkyl groups C1–C5) and their conversion to 5-aminolevulinic acid hydrochloride by acid catalysed hydrolysis is described. As a disadvantage of this procedure description you must consider, that in the final product ammonium chloride and ammonium bromide exist as inorganic impurities and the 5-aminolevulinic acid might occur as the hydrochloride as well as the hydrobromide. Ammonium salts as impurities are only difficult to seperate from the final product—5-aminolevulinic acid hydrochloride/5-aminolevulinic acid hydrobromide—so the task to gain 5-aminolevulinic acid hydrochloride in a purity necessary for medical purposes might be only difficult to solve according to this procedure description.

Behind this background, the procedure proposed for the preparation of 5-chlorolevulinic acid alkyl ester is described.

The proposed procedure starts from known procedures for the production of 5-bromolevulinic acid esters, where by bromination of levulinic acid or levulinic acid methyl ester a mixture of 5-bromo-, 3-bromo-, 3,5-dibromo- and the not brominated levulinic acid ester is the result.

The bromination products are extracted with an organic solvent from an alcohol/water mixture, which you receive after the work-up of the bromination step with water and the extract is stirred after that at temperatures between 20–25° C. and the boiling temperatures of the respective solvents with sodium chloride or saturated aqueous sodium chloride, suitably in the presence of an phase-transfer catalyst. In this reaction step the bromine atoms in the brominated esters are exchanged by chlorine atoms. This exchange takes place within a relatively short time, in a careful manner and quantitative. The mixture of chlorolevulinic esters produced here doesn't show any lachrymatory properties. The exchange of chlorine and bromine by a halogen in the produced pure bromolevulinic alkyl esters or chlorolevulinic alkyl esters can be made in principal also with fluorine and iodine. The exchange of chlorine or bromine can under the conditions of the phase-transfer catalysis also be made with the neat bromination mixture.

Non-toxic and harmless ethyl acetate proved to be a very suitable organic solvent for the bromine/chlorine exchange, which is on top regenerable and can be lead back to the synthesis cycle. As with water only with difficulty or not mixable solvents for the phase-transfer catalysed halogen exchange are also suitable:
ester like:
  butylacetate
  amylacetate
alcohols like.
  butanol
  pentanol
  isobutanol
ethers like:
  di-n-buthyl ether
  diisopropyl ether
  diisoamyl ether
  tert-butyl methyl ether aliphatic and aromatic hydrogen halides like (this solvents are only suitable for the exchange of bromine/chlorine but not for the bromine or chlorine/iodine or fluorine exchange):
  dichloromethane
  tetrachloroethylene
  tetrachloromethane
  1,1-dichloroethane.

As phase-transfer catalysts the following quarternary ammonium salts and quarternary phosphonium compounds can be listed as examples:
  tetrabutyl ammonium bromide
  tetrabutyl ammonium chloride
  tetrabutyl ammonium iodide
  benzyltrimethyl ammonium bromide
  tetrabutyl ammonium hydrogen sulfate
  benzyldimethyl-n-dodecyl ammonium bromide
  trioctylmethyl ammonium chloride (adogen 464)
  ethyltrioctyl phosphonium bromide
  hexadecyltributyl phosphonium bromide
  phase-transfer catalysts which bases on polymers.

With regard to the large-scale production of 5-chlorolevulinic acid alkyl esters the decribed process is superior to all previous processes. The proportion of the produced 5-chlorolevulinic acid alkyl ester in the mixture is equal or higher than 56%. Byproducts are merely 3-chlorolevulinic acid esters (<28%), the 3,5-dichlorolevulinic acid esters (about 8%) and the not converted levulinic acid esters (about 8%).

While doing this the bromination step and the following bromine/chlorine exchange are carried out without changing the reaction vessel.

After the drying and distillation off of the solvent from the chlorination mixtures the residue is purified by means of fractional distillation. In comparison with the brominated products the corresponding chlorinated products have essentially lower boiling points. The 3-chlorolevulinic esters together with the not converted levulinic acid esters always form the first fraction of the distillation followed by the 5-chlorolevulinic esters in the second fraction. The higher chlorinated products have a higher boiling point compared with the mono-chlorinated products and form the third fraction. The mass balance sheet of the distillate in relation to the starting distillation good is always >90%. The fractional distillation is carried out in vacuo, which according to the present invention means, that it is worked with a negative pressure. The yield (in relation to the starting quantity of levulinic acid or levulinic acid methyl ester) of 5-chlorolevulinic acid methyl ester after the distillation is at least 50% (purity>98%).

On the one hand the sequence of the halogenation reactions takes into consideration, that the bromination of the starting compound is more selective than their chlorination. On the other hand the mixture of the chlorinated levulinic acid compounds, which is present after the quantitative halogen exchange, behaves in comparison to the present bromination mixture more stable towards acid catalysed isomerisation because the chlorination products have clearly lower boiling points and therefore the activation of a thermal caused production of hydrogen chloride from the 3,5-dichloro compound is avoided.

In view of a synthesis of the 5-aminolevulinic acid hydrochloride starting from 5-chlorolevulinic acid methylester there is in comparison with the homologue bromine compound an essential advantage, that you produce only sodium chloride as an inorganic by-product when it is converted with sodium azide or other nitrogen nucleophiles, which are used as their sodium salts (for example imides). In organic solvents sodium chloride is practically unsolulable. That means, that this by-product may be removed in a simple manner by filtration and the produced product may be lead directly to the following step practically without the presence of any inorganic impurity. In view of the use of 5-aminolevulinic acid hydrochloride in the medical field this fact is in so far of great importance as in the so produced product only sodium chloride and no other inorganic impurities can be present, which for example in the case of the present sodium chloride would cause a more expensive analytics.

In connection with this it is remarkable, that the 5-chlorolevulinic acid methyl ester can be also selectively produced by means of low temperature crystallisation from the chlorination mixture, which you get from the bromination mixture of levulinic acid or levulinic acid methyl ester in methanol and the subsequent bromine/chlorine exchange, in a gentle manner as already described for the 5-bromolevulinic acid methyl ester. As in the case of the 5-bromolevulinic methyl ester you proceed in the same way by using the same solvents and solvent mixtures and temperatures between −20° C. and −40° C. You get the 5-chlorolevulinic acid methyl ester in 35–38% yield and >98 purity. Impurities are the 3-chlorolevulinic acid methyl ester and the unconverted levulinic acid methyl ester. The 5-chlorolevulinic acid esters of the alcohols with chain lengths of C2–C4 can not be produced by low-temperature crystallisation because no crystallisation occurs under these conditions. The same is valid for the corresponding bromination mixtures of the 5-bromolevulinic acid esters which are produced from alcohols with chain lengths of C2–C4.

The first fraction of the distillation always consists of small amounts of the 5-chlorolevulinic acid ester, the 3-chlorolevulinic acid ester and the unconverted levulinic acid ester. These compounds can be converted in the levulinic acid esters by catalytic hydrogenation in the presence of an hydrogenation catalyst and a non-nucleophilic tertiary amine (for the purpose of catching the generated hydrogen chloride) and can therefore be quantitatively lead back to the bromination step. The used hydrogenation catalyst, preferably palladium on carbon according to the invention, may be regenerated. As solvent suitably the respective alcohol is used, which forms the rest of the ester. Only amine hydrochloride is formed as by-product The used solvents are regenerable. The catalytic hydrogenation of the by-products yields the levulinic acid esters and opens a possibility to regenerate the starting materials and to lead them back into the synthesis cycle. Alternatively, the 3-chloro compounds can be transferred into other synthetic pathways, so that a cost-intensive disposal of the byproducts can be avoided. The solvents and the catalyst are regenerable, only the hydrochloride of a tertiary amine has to be disposed of. The synthesis starts with cheap levulinic acid or the esters thereof, which are available in large quantities on the market and which can be produced on a large scale, for example from waste paper (comp. E. S. Oson, M. R. Kjelden, A. J. Schlag, R. K. Shamma, ACS Symposium Series 2001, 784, 51–63). The 5-chlorolevulinic acid esters which contain ester alkyl groups>C2 can be produced unproblematically and in nearly quantitative yield by means of transesterification of the 5-chlorolevulinic methyl- and ethyl ester using the concerning alcohols according to standard procedures. The 5-chlorolevulinic acid can be produced by means of ester hydrolysis of the 5-chloro levulinic esters according to standard procedures in a high yield.

EXAMPLES

Further details, features and advantages of the present invention can be drawn from the following part of the description. In this part of the description examples are described, which were carried out in the laboratory.

EXAMPLE 1

Preparation of 5-bromolevulinic Acid Methyl Ester from Levulinic Acid

In a threee-necked flask equipped with a mechanical stirrer, a reflux condenser, an internal thermometer and a dropping funnel, to a solution of levulinic acid (600 g, 5.17 mol) in 2400 ml bulk grade methanol bromine (826.2 g, 5.17 mol) was dropped at 20–25° C. during 15 min. Within 1.5 h the reaction temperature rised to 60° C. Afterwards, the color of the solution changed from dark-red to orange within 2 min. At this time the reaction was finished ($^1$H-NMR control). Water was added (2500 ml), which caused the precipitation of a yellowish oil. The oil was separated and the remaining solution was extracted with dichloromethane (3×300 ml). The combined organic extracts were combined with the oil and the resulting mixture was washed with saturated aqueous sodium hydrogen carbonate (3×200 ml) and saturated aqueous sodium chloride (3×200 ml). Drying of the organic layer with $Na_2SO_4$ and distillation of the solvent in vacuo yielded a pale yellow oil consisting of 3-bromolevulinic acid methyl ester (1) (28%), 5-bromolevulinic acid methyl ester (2) (56%), 3,5-dibromolevulinic acid methyl ester (3) (8%) and levulinic acid methyl ester (4) (8%). The composition of the resulting product mixture was monitored by the NMR-spectrum, and the product ratio was calculated from the sum of the integrations of the 5-$CH_2$ (2, 3) and the 5-$CH_3$ (1, 4) signals of the compounds, whereas the sum of the single proton integrations was set to 100%.

Diethyl ether, t-butyl methyl ether and trichloromethane are also suitable organic solvents for the isolation of the products by means of extraction. Best results were otained by the use of trichloromethane, dichloromethane and ethyl acetate.

Diethyl ether/petroleum ether (30–50° C.) 1:1 (4000 ml) was added to the mixture. The resulting solution was cooled down to temperatures between −20 and −40° C. for 2 h while colorless needles or plates crystallised out of the solution. Removal of the mother liquor, subsequent swirling of the remaining crystals with precooled (−20° C.) diethyl ether/petroleum ether (30–50° C.) 1:1 (1000 ml) and removal of the solution yielded 5-bromo levulinic acid methyl ester (400 g, 37%) as colorless crystals, m. p. 12–15° C.

Ethanol, 2-propanol, diisopropyl ether and t-butyl methyl ether/petroleum ether (30–50° C.) 1:1 are also suitable solvents for the preparation of pure 5-bromo levulinic acid methyl ester by means of low-temperature crystallisation. Cyclohexane and the higher-boiling petroleum ether fractions instead of the low-boiling petroleum ether fractions in combination with the ethers mentioned above may also be used as solvents for the purpose of crystallisation. The best results were obtained by using the solvent mixture described according to Example 1.

EXAMPLE 2

Preparation of 5-bromolevulinic Acid Methyl Ester from Levulinic Acid Methyl Ester In a threee-necked flask equipped with a mechanical stirrer, a reflux condenser, an internal thermometer and a dropping funnel, to a mixture of levulinic acid methyl ester (5 g, 38.4 mmol) and bulk grade methanol (30 ml) bromine (6.14 g, 38.4 mmol) was dropped at 20–25° C. during 15 min. Stirring was continued at 20–25° C. After 1.5 h the reaction temperature rose to 35° C. and the color of the solution changed from dark-red to orange within 2 min followed by the decrease of the inner temperature to 20–25° C. At this time the reaction was finished. Water was added (100 ml), which caused the precipitation of a yellowish oil. The oil was separated and the remaining aqueous solution was extracted with dichloromethane (2×30 ml). The combined organic extracts were added to the oil and the resulting mixture was washed with saturated aqueous sodium hydrogen carbonate (2×20 ml) and saturated aqueous sodium chloride (2×20 ml). Drying of the organic layer with $Na_2SO_4$ and distillation of the solvent in vacuo yielded a pale yellow oil (7.56 g) consisting of 3-bromolevulinic acid methyl ester (1) (28%), 5-bromolevulinic acid methyl ester (2) (56%), 3,5-dibromolevulinic acid methyl ester (3) (8%) and levulinic acid methyl ester (4) (8%). Diethyl ether/petroleum ether (30–50° C.) 1:1 (50 ml) was added to the mixture. The resulting solution was then cooled down to temperatures between –20 and –40° C., and within 2 h colorless needles or plates crystallised out of the solution. Removal of the mother liquor, subsequent swirling of the remaining crystals with precooled (–20° C.) diethyl ether/petroleum ether (30–50° C.) 1:1 (20 ml) and removal of the solution yielded 5-bromolevulinic acid methyl ester (2.9 g, 36%) as colorless crystals, m. p. 12–15° C.

EXAMPLE 3

Preparation of Levulinic Acid Methyl Ester from the Remaining Mother Liquors, Which were Obtained by Low-Temperature Crystallisation of 5-bromolevulinic Acid Methyl Ester According to Example 1, Consisting of 3-bromolevulinic Acid Methyl Ester, 5-bromolevulinic Acid Methyl Ester, 3,5-dibromolevulinic Acid Methyl Ester and Levulinic Acid Methyl Ester Distillation of the solvent from the combined mother liquors obtained from the low-temperature crystallisation of 5-bromolevulinic acid methyl ester according to Example 1 in vacuo afforded a mixture consisting of 3-bromolevulinic acid methyl ester (61%), 5-bromolevulinic acid methyl ester (23%), 3,5-dibromolevulinic acid methyl ester (8%) and levulinic acid methyl ester (8%). The mixture (5 g) was dissolved in bulk grade methanol (20 ml), a hydrogen catalyst (palladium on carbon) was then added and the mixture was hydrogenated for 5 h while passing in hydrogen at a pressure of 20 bar at 20–25° C. By monitoring the hydrogenation, it was found that the reaction was completed after 5 h ($^1$H-NMR, $^{13}$C-NMR) and besides hydrogen bromide only levulinic acid methyl ester has been formed. Water was added (20 ml) and the resulting mixture was extracted with dichloro methane (3×20 ml). The combined organic extracts were washed with saturated aqueous sodium hydrogen carbonate (3×10 ml) and saturated aqueous sodium chloride. Drying of the organic layer with $Na_2SO_4$, followed by distillation of the solvent in vacuo yielded 2.5 g (80%) levulinic acid methyl ester. The obtained product may be used for the preparation of 5-bromolevulinic acid methyl ester according to Example 2. The further purification of the obtained levulinic acid methyl ester by distillation is not necessary, so that the raw-product may be directly lead back to the bromination step after removing the hydrogen bromide for the most part.

EXAMPLE 4

Preparation of 5-chlorolevulinic Acid Methyl Ester, 5-chlorolevulinic Acid Ethyl Ester, 5-chlorolevulinic Acid Propyl Ester and 5-chlorolevulinic Acid n-butyl Ester from Bromination Mixtures of the Corresponding Bromination Products by Phase-transfer Catalysed Bromine/chlorine Exchange. General Method for the Preparation of the 5-chlorolevulinic Acid methyl-, -ethyl-, -propyl- and -n-butyl Esters In a threee-necked flask equipped with a mechanical stirrer, a reflux condenser, an internal thermometer and a dropping funnel, to a pre-cooled solution (10° C.) of levulinic acid (1 mol) or levulinic acid methyl ester (1 mol) and the corresponding alcohol (400 ml) which forms the alkyl chain of the prepared ester, bromine (1 mol) was added. Stirring was continued until the initial color of the mixture changed from dark-red to orange or yellow. While stirring, the mixture was allowed to attain 20–25° C. The reaction was finished when decolorisation of the mixture occured. Water was added (400 ml) which caused precipitation of an oil. The oil was separated and the remaining aqueous solution was extracted with a total of 200 ml of ethyl acetate. The aqueous layer was separated and to the organic layer were added saturated aqueous sodium chloride (1000 ml) and trioctyl methy ammonium chloride (10 g). Stirring was continued at 20–25° C. or under reflux until the reaction was virtually complete (DC, $^1$H-NMR). If necessary, the aqueous sodium chloride was replaced by a freshly prepared solution. The organic layer was separated, washed with water (100 ml), dried with $Na_2SO_4$, and subsequently the solvent was distilled in vacuo. In a claisen apparatus, the residue was distilled in vacuo (10 mm, except the 5-chlorolevulinic acid n-butyl ether, b.p. 158° C. at 10 mm). In all cases a first fraction was taken, which contained the unconverted levulinic acid alkyl ester, the 3-chlorolevulinic acid alkyl ester and small amounts of the desired 5-chlorolevulinic acid alkyl ester. The residue of the distillation consisted of small amounts of both 5-chlorolevulinic acid alkyl ester and 3,5-dichlorolevulinic acid alkyl ester.

Differing from the general method, the 5-chlorolevulinic acid n-butyl ester was prepared by washing the bromination mixture acid-free with water. The resulting solution of the bromination mixture in n-butanol was supplied to the bromine/chlorine exchange step by phase-transfer catalysis. Afterwards, the process was continued as described according to the general method. The distillation was carried out at $5 \cdot 10^{-2}$ mm.

EXAMPLE 5

Preparation of 5-chlorolevulinic acid methyl ester from a mixture of 3-chloro-, 5-chloro-, 3,5-dichlorolevulinic acid ethyl ester and levulinic acid methyl ester consisting of the same product ratio, which is obtained by the bromination of both levulinic acid and levulinic acid methyl ester according to the Examples 1 and 2.

According to Example 4, a chlorination mixture of levulinic acid methyl ester was prepared. After the work-up as described, the solvent was distilled in vacuo. The product ratio of 5-chlorolevulinic acid methyl ester: 3,5-dichlorolevulinic acid methyl ester:3-chlorolevulinic acid methyl ester:levulinic acid methyl ester agreed with that found for the corresponding bromination products according to Example 1 and was calculated by means of the integration of the characteristic NMR proton signals.

Diethyl ether/petroleum ether (30–50° C.) 1:1 (800 ml) was added to the mixture of the raw-products and the mixture was kept at temperatures between −20° C. and −40° C. for 4 h while the desired product crystallised out of the solution as colorless needles. Removal of the mother liquor, subsequent swirling of the remaining crystals with pre-cooled (−20° C.) diethyl ether/petroleum ether (30–50° C.) 1:1 (200 ml) and removal of the solution yielded 5-chlorolevulinic acid methyl ester (62 g, 38%) as colorless crystals, m. p. 8–13° C. The crystallisation may also occur successfully using the additional listed solvents described in Example 1.

The NMR data of the product agree with the data of the 5-chlorolevulinic acid methyl ester obtained according to Example 4. The product, which is prepared by this method is obtained in >98% purity.

EXAMPLE 6

Catalytic Hydrogenation of the Residue of the Low-Temperature Crystallisation According to Example 5—Recycling of the Levulinic Acid Methyl Ester Distillation of the solvent from the combined mother liquors obtained from the low-temperature crystallisation of 5-bromo levulinic acid methyl ester according to Example 1 in vacuo afforded a mixture consisting of 3-bromolevulinic acid methyl ester (61%), 5-bromolevulinic acid methyl ester (23%), 3,5-dibromolevulinic acid methyl ester (8%) and levulinic acid methyl ester (8%). The mixture (5 g) was dissolved in bulk grade methanol (20 ml), a hydrogen catalyst (palladium on carbon) and 2.45 g of triethyl amine were added and the mixture was hydrogenated for 5 h while passing in hydrogen at a pressure of 20 bar at 20–25° C. The reaction was completed after 5 h ($^1$H-NMR). The catalyst was then filtered off from the reaction mixture, and after the distillation of the solvent in vacuo, ethyl acetate was added and the solid was filtered off. Distillation of the sovent and the residue in vacuo afforded 2.96 g (95%) levulinic acid methyl ester.

EXAMPLE 7

Examplary Transesterification of 5-chlorolevulinic Acid Methyl Ester with 1-propanol To a solution of 5-chlorolevulinic acid methyl ester (10 g) in 1-propanol (50 ml) and concentrated sulfuric acid was added (0.5 ml) and the reaction mixture was refluxed for 3 h. Thereafter, the methanol and the excess 1-propanol were distilled in vacuo. Dichloromethane was added to the residue and the organic layer was washed with saturated aqueous sodium hydrogen carbonate and water. Drying of the organic layer with $Na_2SO_4$ followed by distillation of the solvent in vacuo yielded 5.4 g (quant.) 5-chlorolevulinic acid propyl ester. The NMR data agreed with the data for the product obtained according to Example 4.

EXAMPLE 8

Examplary conversion of the 5-chlorolevulinic acid alkyl esters with sodium azide to the 5-azidolevulinic acid alkyl esters. General method for the preparation of the 5-azido levulinic acid methyl-, -ethyl-, -propyl- and n-butyl esters.

The 5-chlorolevulinic acid alkyl esters (1 g) were dissoled in bulk grade acetone (3 ml), the stoechiometric amount of sodium azide was added and the reaction mixture was stirred at 20–25° C. for 10 h. Filtration of the separated sodium chloride from the reaction mixture and distillation of the solvent in vacuo afforded the desired 5-azidolevulinic acid alkyl esters as yellow to dark-yellow oils in quantitative yield (purity>99%). No byproducts were formed.

EXAMPLE 9

Examplary conversion of 5-aminolevulinic acid hydrochloride by catalytic reduction of the 5-azidolevulinic acid alkyl esters and subsequent hydrolysis of the intermediate 5-aminolevulinic acid alkyl ester hydrochlorides. General method for the preparation and the hydrolysis of the intermediate 5-aminolevulinic acid alkyl ester hydrochlorides, which contain ester alkyl chains C1–C3 by catalytic hydrogenation of the alkyl esters and subsequent acid catalysed hydrolysis with formation of 5-aminolevulinic acid hydrochloride.

5-Azidolevulinic acid alkyl ester (1 g) was dissolved in a mixture of the alcohol (10 ml), which represents the alkyl chain in the final ester and aqueous hydrochloric acid (2 mol/l). A hydrogenation catalyst (palladium on carbon) was added and the mixture was hydrogenated for 3 h while passing in hydrogen at a pressure of 1–6 bar. By monitoring the hydrogenation, it was found that the hydrogenation was completed quantitatively after 3 h ($^1$H-NMR). The hydrogenation is accompanied by an increase of the reaction temperature to 35° C. The reaction is complete, when the reaction temperature reaches 20–25° C. again ($^1$H-NMR). The catalyst was then filtered off from the reaction mixture, and the alcohol was distilled in vacuo. A small amount of activated charcoal and aqueous hydrochloric acid (10 ml, 6 mol/l) were added and subsequently the reaction mixture was refluxed for 5 h. The activated charcoal was then filtered off, and both the water and the alcohol were removed by distillation in vacuo. While stirring, to the nearly colorless and viscous residue 2-propanol (20 ml) was added. After one minute a white and crystalline solid abruptly precipitated. The solid was filtered off using a glass frit Washing of the solid with little 2-propanol and drying of the crystals in vacuo yielded colorless crystals (85–90%, m. p. 150–151° C.) consisting of pure 5-aminolevulinic acid hydrochloride When the batch size was increased starting from 75 g of 5-azidolevulinic acid alkyl ester the same result was obtained. The physical and spectroscopical data agree with those found in the literature (H.-J. Ha, S.-K. Lee, Y.-J. Ha, J. W. Park, Synth. Comm. 1994, 24(18), 2557–2562).

EXAMPLE 10

Examplary reaction of 5-chlorolevulinic acid alkyl esters with hexamethylene tetramine (urotropine) to the corresponding 5-urotropiniumlevulinic acid alkyl esters. Subsequent acid catalysed hydrolysis of the 5-urotropiniumlevulinic acid alkyl esters resulting in the formation of 5-amino levulinic acid hydrochloride.

5-Chlorolevulinic acid alkyl ester (5 g) was dissolved in ethanol (50 ml) and the calculated stoechiometric amount of hexamethylene tetramine(urotropine) was added. Afterwards, the reaction mixture was refluxed for 2 h. Filtration of the precipitated ammonium chloride and evaporation of the alcohol and the volatile formaldehyde diacetale in vacuo afforded a yellow to brown residue. The residue was dissolved in methanol and subsequently, the 5-aminolevulinic acid hydrochloride was precipitated as a white and microcrystalline solid by addition of diethyl ether. Filtration and subsequent drying of the solid in vacuo yielded pure 5-aminolevulinic acid hydrochloride (75–85%, m p. 150–151° C.). The NMR data of the obtained product agree with those found in the literature (H.-J. Ha, S.-K. Lee, Y.-J. Ha, J. W. Park, Synth. Comm. 1994, 24(18), 2557–2562).

What is claimed is:

1. A method for obtaining 5-bromo-levulinic acid methyl ester, comprising the steps of:
   brominating a member selected from the group consisting of levulinic acid, levulinic acid methyl ester and a combination thereof, for producing a bromination mixture containing a 5-bromolevulinic acid methyl ester;
   dissolving said bromination mixture in an organic solvent or solvent mixture for forming a solution;
   cooling said solution for crystallizing 5-bromolevulinic acid methyl ester from said solution and obtaining crystalline 5-bromolevulinic acid methyl ester; wherein said cooling step is carried out at a temperature lower than −20° C. and,
   draining off said solution with any remaining said bromination mixture for isolating said crystallizing 5-bromolevulinic acid methyl ester, thereby obtaining 5-bromolevulinic acid methyl ester.

2. The method for obtaining 5-bromo-levulinic acid methyl ester according to claim 1, wherein said organic solvent used in said step of dissolving said bromination mixture is a member selected from the group consisting of ethanol, 2-propanol, diisopropyl ether and a combination thereof.

3. The method for obtaining 5-bromo-levulinic acid methyl ester according to claim 1, wherein said solvent mixture used in said step of dissolving said bromination mixture is a member selected from the group consisting of diethyl either with petroleum ether fractions, t-butyl methyl either with petroleum ether, diethyl ether with cyclohexane, t-butyl methyl either with cyclohexane and a combination thereof.

4. The method for obtaining 5-bromo-levulinic acid methyl ester according to claim 1, further comprising the steps of:
   catalytic hydrogenating the remaining said bromination mixture to levulinic acid methyl ester; and,
   brominating said levulinic acid methyl ester for obtaining additional said bromination mixture containing 5-bromolevulinic acid methyl ester.

5. The method for obtaining 5-bromo-levulinic acid methyl ester according to claim 4, wherein palladium on carbon as a catalyst in said step of catalytic hydrogenating.

6. The method for obtaining 5-bromo-levulinic acid methyl ester according to claim 1, wherein said cooling step is carried out at a temperature between −20° C. to −40° C.

7. A method for obtaining 5-chloro-levulinic acid methyl ester, comprising the steps of:
   chlorinating a member selected from the group consisting of levulinic acid, levulinic acid methyl ester and a combination thereof, for producing a chlorination mixture containing a 5-chlorolevulinic acid methyl ester;
   dissolving said chlorination mixture in an organic solvent or solvent mixture for forming a solution;
   cooling said solution for crystallizing 5-chlorolevulinic acid methyl ester from said solution and obtaining crystalline 5-chlorolevulinic acid methyl ester; and,
   draining off said solution with any remaining said chlorination mixture for isolating said crystallizing 5-chlorolevulinic acid methyl ester, thereby obtaining 5-chlorolevulinic acid methyl ester.

8. The method for obtaining 5-chloro-levulinic acid methyl ester according to claim 7, wherein said organic solvent used in said step of dissolving said chlorination mixture is a member selected from the group consisting of ethanol, 2-propanol, diisopropyl ether and a combination thereof.

9. The method for obtaining 5-chloro-levulinic acid methyl ester according to claim 7, wherein said solvent mixture used in said step of dissolving said chlorination mixture is a member selected from the group consisting of diethyl either with petroleum ether fractions, t-butyl methyl either with petroleum ether, diethyl ether with cyclohexane, t-butyl methyl either with cyclohexane and a combination thereof.

10. The method for obtaining 5-chloro-levulinic acid methyl ester according to claim 7, further comprising the steps of:
    catalytic hydrogenating the remaining said chlorination mixture to levulinic acid methyl ester; and,
    chlorinating said levulinic acid methyl ester for obtaining additional said chlorination mixture containing 5-chloro-levulinic acid methyl ester.

11. The method for obtaining 5-chloro-levulinic acid methyl ester according to claim 10, wherein palladium on carbon as a catalyst in said step of catalytic hydrogenating.

12. The method for obtaining 5-chloro-levulinic acid methyl ester according to claim 7, wherein said cooling step is carried out at a temperature lower than −20° C.

13. The method for obtaining 5-chloro-levulinic acid methyl ester according to claim 7, wherein said cooling step is carried out at a temperature between −20° C. to −40° C.

14. A method for obtaining 5-chlorolevulinic acid alkyl ester from a bromination mixture containing 5-bromolevulinic acid alkyl ester, comprising the steps of:
    brominating a member selected from the group consisting of levulinic acid, levulinic acid methyl ester and a combination thereof, for forming a bromination mixture containing 5-bromolevulinic acid alkyl ester;
    halide exchanging via a phase-transfer catalyzed reaction of said bromination mixture with an alkali chloride for obtaining a mixture containing 5-chlorolevulinic acid alkyl ester; and,
    isolating a 5-chlorolevulinic acid alkyl ester from said mixture containing said 5-chlorolevulinic acid alkyl ester via fractional distillation in vacuo.

15. The method for obtaining 5-chlorolevulinic acid alkyl ester from a bromination mixture containing 5-bromolevulinic acid alkyl ester according to claim 14, wherein said 5-bromolevulinic acid alkyl ester is member selected from the group consisting of 5-bromolevulinic acid methyl ester, 5-bromolevulinic acid ethyl ester and a combination thereof.

16. The method for obtaining 5-chlorolevulinic acid alkyl ester from a bromination mixture containing 5-bromolevulinic acid alkyl ester according to claim 14, wherein trioctylmethyl ammonium chloride is used as a catalyst for said phase-transfer catalyzed reaction of said halide exchanging step.

* * * * *